(12) United States Patent
Adami et al.

(10) Patent No.: US 7,176,692 B2
(45) Date of Patent: Feb. 13, 2007

(54) MEASURING PROBE FOR POTENTIOMETRIC MEASUREMENTS

(75) Inventors: Jean-Nicolas Adami, Zurich (CH); Philippe Ehrismann, Uster (CH); Markus Bernasconi, Buchs (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 11/157,366

(22) Filed: Jun. 21, 2005

(65) Prior Publication Data

US 2006/0001431 A1 Jan. 5, 2006

(30) Foreign Application Priority Data

Jun. 22, 2004 (EP) .................................. 04102877

(51) Int. Cl.
G01N 27/04 (2006.01)
G01N 27/26 (2006.01)
G01R 27/08 (2006.01)

(52) U.S. Cl. ...................... 324/446; 324/693; 204/400

(58) Field of Classification Search ................ 324/439, 324/446, 693, 691, 690, 722; 204/420, 435, 204/433, 400
See application file for complete search history.

(56) References Cited

U.S. PATENT DOCUMENTS

| | | | | |
|---|---|---|---|---|
| 2,563,062 A | | 8/1951 | Perley ........................ 204/195 |
| 4,217,194 A | * | 8/1980 | Lubbers et al. ........ 204/192.15 |
| 4,822,456 A | * | 4/1989 | Bryan ........................ 205/789 |
| 5,016,201 A | * | 5/1991 | Bryan et al. ................ 700/267 |
| 5,221,456 A | * | 6/1993 | Benton et al. .............. 204/416 |
| 5,316,649 A | | 5/1994 | Kronberg .................... 204/435 |
| 5,795,631 A | * | 8/1998 | Parkansky et al. ......... 428/34.1 |
| 2003/0132755 A1 | | 7/2003 | Feng et al. .................. 324/438 |
| 2003/0150726 A1 | * | 8/2003 | West et al. ................. 204/433 |
| 2003/0178305 A1 | * | 9/2003 | Catalano et al. ............ 204/433 |
| 2004/0180391 A1 | * | 9/2004 | Gratzl et al. .................. 435/14 |
| 2005/0082167 A1 | * | 4/2005 | Iwamoto et al. ............ 204/433 |

FOREIGN PATENT DOCUMENTS

| | | |
|---|---|---|
| GB | 2 245 707 | 8/1992 |
| JP | 57103044 | 6/1982 |

* cited by examiner

*Primary Examiner*—Andrew H. Hirshfeld
*Assistant Examiner*—Hoai-An D. Nguyen
(74) *Attorney, Agent, or Firm*—Standley Law Group LLP

(57) ABSTRACT

A measuring probe for potentiometric measurements has a housing (2) formed of an electrically insulating material that encloses at least one hollow space (8, 10) containing a half-cell element defining a first electrode. At least one additional electrode (12) is provided on a portion (4) of the housing adapted for immersion in a measuring solution (6) and is connected to a contact terminal (K3) that is arranged outside of the immersible portion (4). Each additional electrode (12) is defined by an electrically conductive coating (14) applied to the outside of the housing (2).

29 Claims, 3 Drawing Sheets

MEASURING PROBE FOR POTENTIOMETRIC MEASUREMENTS

TECHNICAL FIELD

The invention relates to a measuring probe as well as to a device for performing potentiometric measurements and a method of monitoring a measuring probe for potentiometric measurements.

BACKGROUND OF THE ART

A measuring probe of the same generic type as the present invention is described in U.S. Pat. No. 6,894,502 B2, issued to Feng, et al., specifically FIG. 1 therein and in the assessment of the prior art. The practice of equipping potentiometric measuring probes with an external pin-shaped additional electrode (referred to as a "solution ground" in English terminology) serves, among other functions, to diagnose the condition of the sensor, for example to measure and monitor the resistance of a diaphragm or a glass membrane. Furthermore, a measuring solution or process solution in which the measuring probe is immersed can be set at ground potential or another defined potential by means of an additional electrode.

It is a disadvantage of the known state-of-the-art measuring probes that the additional pin-shaped electrode which is arranged at the bottom part of the housing requires an expensive fastening process in the course of the production process of the probes, for example by fusing the additional electrode into the housing. Furthermore, the type of additional electrode that is known from the existing state of the art, where the additional electrode protrudes from the housing, is configured as a mechanically exposed component of the measuring probe, requiring additional space and also having a tendency to get damaged.

The task set for the present invention is to improve a measuring probe of the same general kind as the probes described above, in particular by avoiding their disadvantages. A further objective of the invention is to propose an improved device for performing potentiometric measurements. The invention further has the objective to provide an improved method of monitoring a measuring probe.

SUMMARY OF THE INVENTION

The foregoing tasks are solved by the measuring probe as defined in the appended claims, the device also defined therein, and the method defined therein.

The measuring probe according to the invention has a housing that is formed of an electrically insulating material and has at least one hollow space containing a half-cell element. The measuring probe further has at least one additional electrode that is arranged on an immersible housing portion designed to be immersed in a measuring- or process solution. The additional electrode is connected to a contact terminal that is arranged in a place on the measuring probe outside of the immersible portion. By configuring the additional electrode as an electrically conductive coating applied to the outside of the housing, one obtains a compact design of the measuring probe without protruding or otherwise exposed components. In addition, the process of applying the additional electrode can be performed with coating techniques that are well under control, are tried and proven, suitable for large-scale production, and will therefore lastly also provide a cost advantage.

The inventive device for performing potentiometric measurements includes a measuring probe according to the invention as well as a measurement converter that can be connected to each half-cell element of the measuring probe as well as to the electrical contact terminal of each additional electrode. The measurement converter further has means for setting a defined potential at an additional electrode and/or means for determining a characteristic electrical quantity that exists between an additional electrode and another part of the device. Accordingly, when the measuring probe is immersed in a measuring- or process solution, the device can on the one hand be used to set the solution at ground potential, or to set it at the aforementioned defined potential. On the other hand, it can be used to determine different kinds of characteristic quantities that exist between the coating and another part of the device. This includes not only characteristic quantities for diagnosing the condition of the sensor, in particular diaphragm resistances and membrane resistances, but also measurements of, e.g., redox potentials, provided that the measuring probe includes a half-cell element that is usable as a reference electrode.

Advantageous embodiments of the invention are defined in the dependent claims.

The connection between the coating and the associated electrical contact terminal can be realized in different ways, for example as a clamped connection. However, an advantageous solution is to use a solder connection between the contact terminal and the coating, which represents a simple, cost-effective and reliable kind of electrical contact.

In principle, a number of different geometrical shapes could be considered for the coating. The latter can in particular be configured as a coating strip in the lengthwise direction of the housing, or running like a ring around the housing. In an exemplary embodiment, the coating surrounds substantially the entire housing and thereby constitutes an effective electrical screen for the measuring probe. Of course some individual parts of the measuring probe housing have to remain uncoated for functional reasons. Specifically the diaphragm of a reference electrode and the glass membrane of a pH electrode need to be kept free of the coating. It is possible to configure the coating as a raster-like pattern which, in spite of the perforations, provides an effective electrical screen in the manner of a Faraday cage. The latter configuration is used to particular advantage in industrial applications where there is electromagnetic interference, because the electrical screen prevents the occurrence of spurious signals and improves the stability of the measuring signal. As a further benefit, the comparatively large surface of the additional electrode also allows the measurement of large resistances, which represents a considerable advantage particularly for the diagnosis of the sensor condition.

While electrically conductive coatings above a certain thickness necessarily have no transparency, it is possible to preserve a certain level of transparency if the coating thickness is kept comparatively small. Keeping the coating transparent has the significant advantage that the interior of the measuring probe remains visible, even in the aforementioned case where the coating extends completely around the probe, as it will be unnecessary to provide an inspection window in the coating. The visual inspection of the interior of the probe is important in many types of probes in order to determine the condition of the electrodes, for example in reference electrodes that are filled with a saturated electrolyte.

Although different kinds of electrically insulating materials can be considered for the housing, it is of advantage if the housing is formed of glass, in particular because the deposition of the additional electrode can be accomplished with well known coating methods.

The coating is preferably applied by means of a deposition from the gaseous phase, a technology that includes in particular the techniques known as physical vapor deposition (PVD) and chemical vapor deposition (CVD). Besides, the use of deposition methods of this kind is not limited to glass housings.

The choice for the coating includes a variety of materials that are generally known as electrode materials. It is particularly advantageous if the coating is made of platinum. Platinum is well suited for soldering, it has an excellent ability to stand up to chemical, thermal and mechanical conditions, and it is furthermore suitable for the measurement of redox potentials. On the other hand, if the probe is to be used for the determination of metal ion concentrations, a coating of the respective metal is required.

In an advantageous embodiment of the measuring probe, an adhesion-enhancing layer is put between the housing and the coating, whereby an undesirable detachment of the coating can be avoided.

Among other criteria, the choice of material for the adhesion-enhancing layer also depends on the coating, with a selection to be made between titanium, chromium molybdenum, tantalum or tungsten. In some cases, gold or palladium may be added to the adhesion-enhancing layer. Titanium is a particularly preferred choice for the adhesion-providing interface between glass and platinum, because titanium is considered risk-free for applications in biotechnology.

The kind of half-cell element that is used in the measuring probe depends on the intended application. The half-cell element can in particular be configured as a measuring electrode, for example as a glass electrode for pH measurements or as an ion-sensitive ISFET sensor. The half-cell element can further be configured as a reference electrode. As a further possibility, the measuring probe can be configured as a single-rod measuring chain, containing for example a pH electrode together with a reference electrode.

In a preferred further developed embodiment of the measuring probe, the latter is designed in particular for the determination of the electrical conductivity in a measuring medium. To perform this function, the measuring probe has two additional electrodes that are arranged in different parts of the immersible portion of the probe. The additional electrodes are connected to respective contact terminals, and the distance between the additional electrodes defines a measuring length for the measurement of the electrical resistance or the electrical conductivity.

A method of monitoring a measuring probe for potentiometric measurements involves the use of a measuring probe and a measurement converter, wherein the measuring probe includes a housing formed of electrically insulating material with at least one cavity containing a half-cell element and with at least one additional electrode constituted by an electrically conductive coating that is applied to the outside of the housing. The additional electrode is arranged on an immersible portion of the housing which is designed for immersion in a measuring solution. An electrical contact terminal is arranged outside of the immersible portion and connected to the additional electrode. The measurement converter is connected to each of the half-cell elements of the measuring probe and also to the electrical contact terminal of each additional electrode. The method is distinguished by the fact that a characteristic electrical quantity is measured between an additional electrode and another part of the device.

The measurement converter can in particular have the capability to set the additional electrode at a defined electrical potential.

By contacting the appropriate terminals of the measurement converter, it is possible to perform a resistance measurement between the contact terminal of the reference electrode and a contact terminal of the additional electrode for the purpose of determining the diaphragm resistance. As a further possibility, a resistance measurement can be made between the contact terminal of the measuring electrode and the contact terminal of the additional electrode for the purpose of determining the resistance of the glass membrane.

BRIEF DESCRIPTION OF THE DRAWINGS

Embodiments of the invention are described hereinafter in more detail with reference to the drawings, wherein.

DETAILED DESCRIPTION OF A PREFERRED EMBODIMENT

Identical features in the different figures have the same reference symbols. The thickness of the coatings in some parts of the drawings is strongly exaggerated for the sake of clarity.

Figure 1:
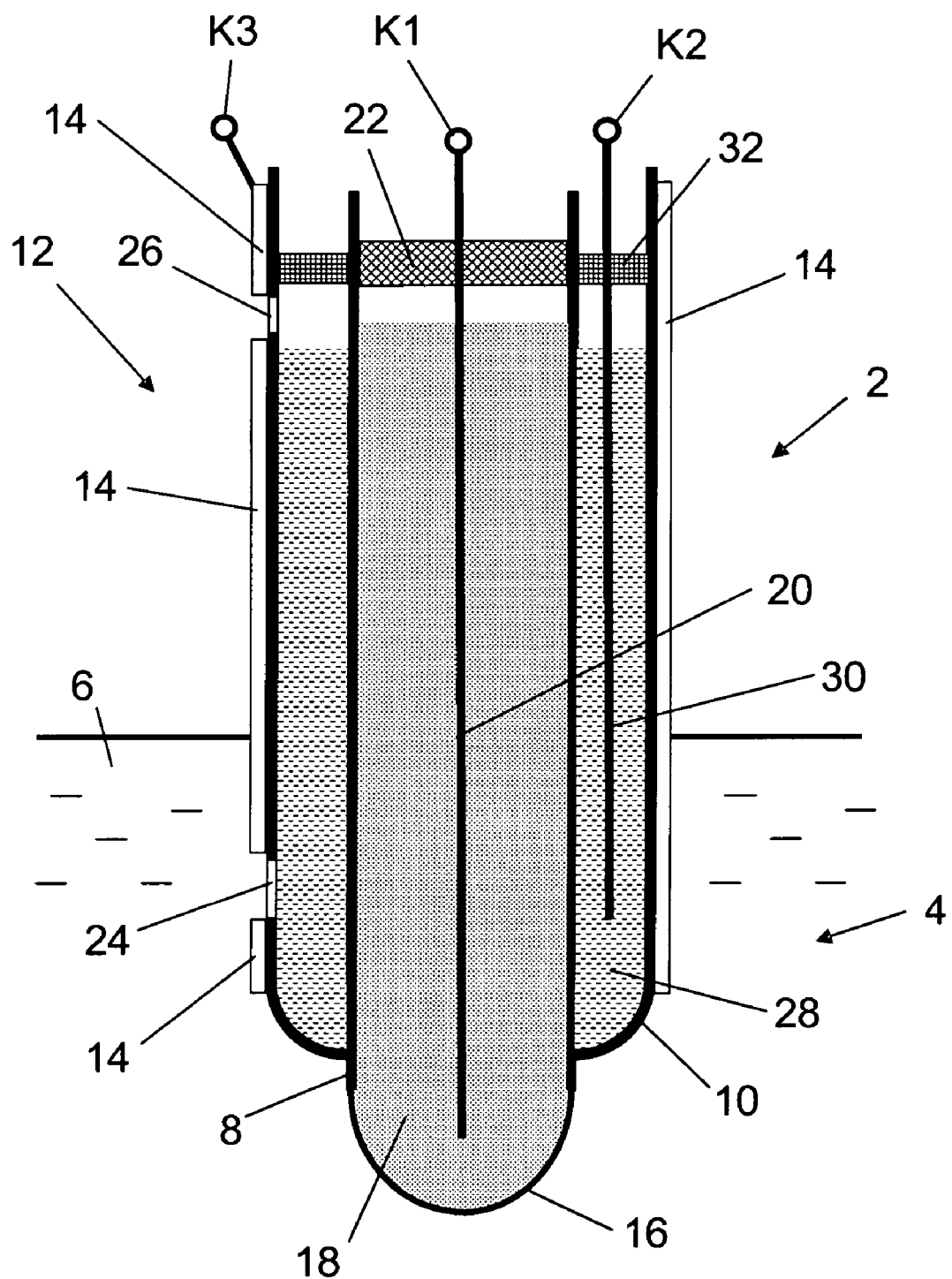
FIG. 1 represents a lengthwise sectional view of a measuring probe that is configured as a single-rod measuring chain.

The measuring probe shown in FIG. 1 has a tubular housing 2 of glass or polymer whose lower end 4 is immersed in a measuring medium 6. The probe housing 2 encloses a central chamber 8 as well as a ring chamber 10 that is arranged concentrically around the central chamber 8. The central chamber 8 contains a first half-cell element configured as a glass electrode, while a second half-cell element configured as a reference electrode is accommodated in the ring chamber 10. The ring chamber 10 carries an electrically conductive coating 14 on the outside, which functions as an additional electrode 12.

The arrangement of the two half-cell elements is known in principle and will be described below only for the purpose of explaining the entire measuring probe.

The protruding lower end of the central chamber 8 is configured as a convexly rounded glass membrane 16 that is made of a so-called pH glass. Furthermore, the central chamber 8 contains an inner buffer solution 18, for example an aqueous acetic acid and acetate buffer solution containing potassium chloride, in which a first conductor element 20 is immersed, for example a silver wire. The latter passes through a fused header 22 (not shown in detail) at the upper end of the central chamber 8 to a measuring contact terminal K1.

The terms "upper" and "lower" in the present context relate to portions of a measuring probe that is immersed in a measuring medium, where the measuring probe is oriented approximately perpendicular to the surface of the measuring medium, as shown for example in FIG. 1. With a different position of the measuring probe, the terms "upper" and "lower" should be adapted accordingly.

In the immersed area 4, the ring chamber 10 has a diaphragm 24 in the shape of a circular disk, and there is a refill opening 26 in the uppermost portion. The ring chamber 10 furthermore contains a reference electrolyte solution 28, for example a saturated potassium chloride solution, in which a silver wire with a coating layer of silver chloride is immersed, serving as a second conductor element 30. The latter passes through an upper closure part 32 of the ring chamber 10 to the outside where it ends in a reference contact terminal K2.

The electrically conductive coating 14 in the illustrated example covers substantially the entire exterior wall surface of the ring chamber 10, but leaves the diaphragm 24 as well as the refill opening 26 uncovered. The uppermost part of the coating 14 is connected to an additional contact terminal K3, the latter being advantageously soldered to the coating 14.

It should be understood that other configurations are possible besides the measuring probe shown in the drawing. Specifically, an electrically conductive coating which functions as an additional electrode could be applied to an individual half cell, for example to a glass electrode or to a reference electrode, instead of a single-rod measuring chain.

Furthermore, the illustrated arrangement can be modified in numerous ways. For example, the glass membrane can have a different shape, such as a spherical membrane or a needle membrane, and the diaphragm can be configured as a ring diaphragm running in a circle. However, the reference electrode can also be designed as a gel electrode with an open fluid passage, i.e., without a diaphragm.

Figure 2:
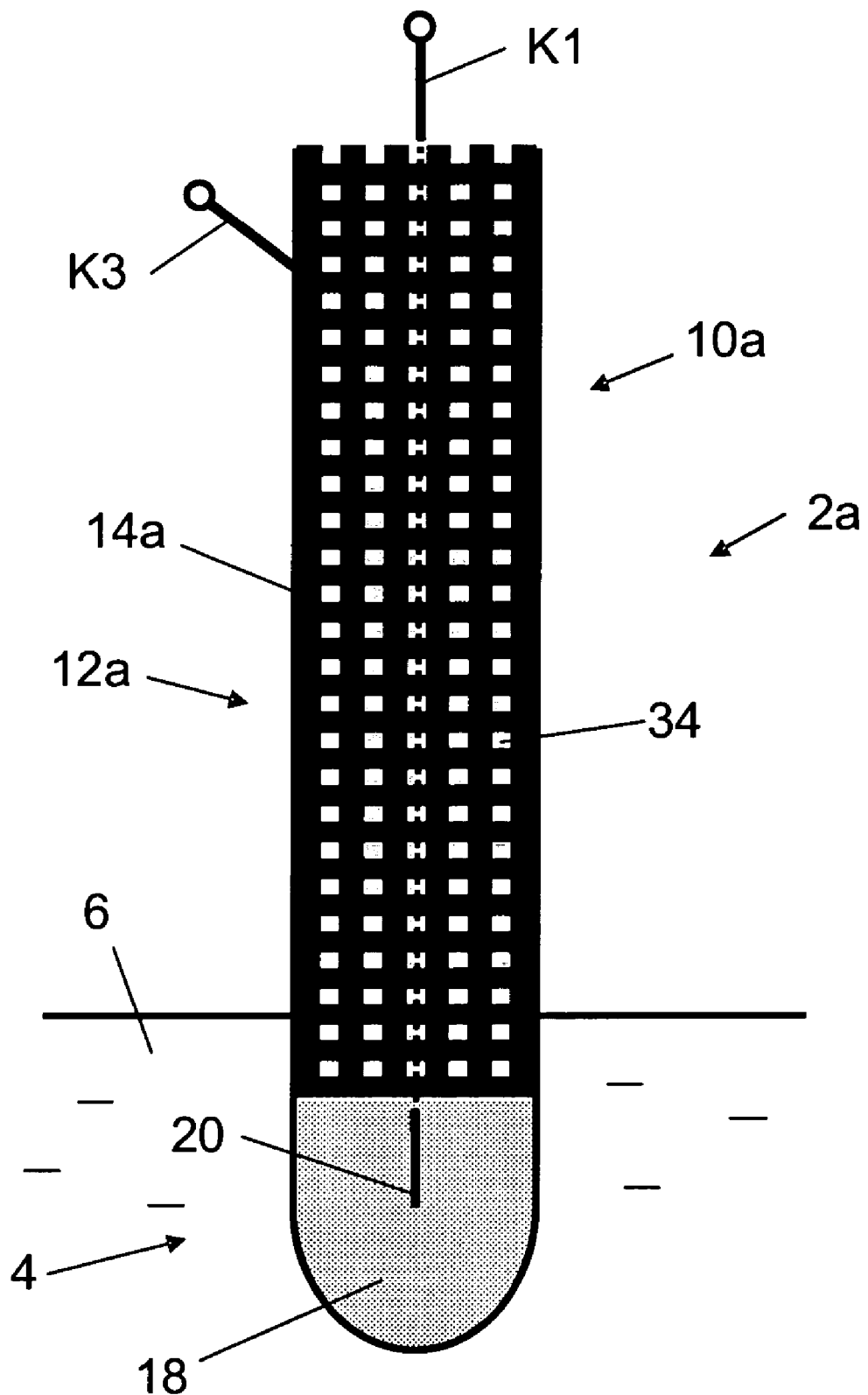
FIG. 2 represents a side view of a measuring probe that is equipped with a raster-like additional electrode.

The measuring probe shown in FIG. 2 includes a pH measuring probe with a housing 2a whose lower end 4 is immersed in a measuring medium 6. The sensor chamber 10a that is formed by the housing 2a contains an inner buffer solution 18 in which a silver wire is immersed which functions as a conductor element 20. The latter passes through an upper closure part (not shown in detail) of the sensor chamber 10a to the outside, ending in a measuring contact terminal K1. As shown in FIG. 2, the sensor probe housing 2a is equipped with an additional electrode 12a that is constituted by a raster-like coating 14a with a large number of small perforations 34. The coating 14a leaves a lower portion of the immersed area 4 uncovered, but otherwise surrounds substantially the entire probe housing 10a. The uppermost part of the coating 14a is soldered to an additional contact terminal K3. The raster-like coating 14a has the effect of a Faraday cage and thus represents an effective screen while still permitting a visual inspection of the interior of the probe.

Figure 3:
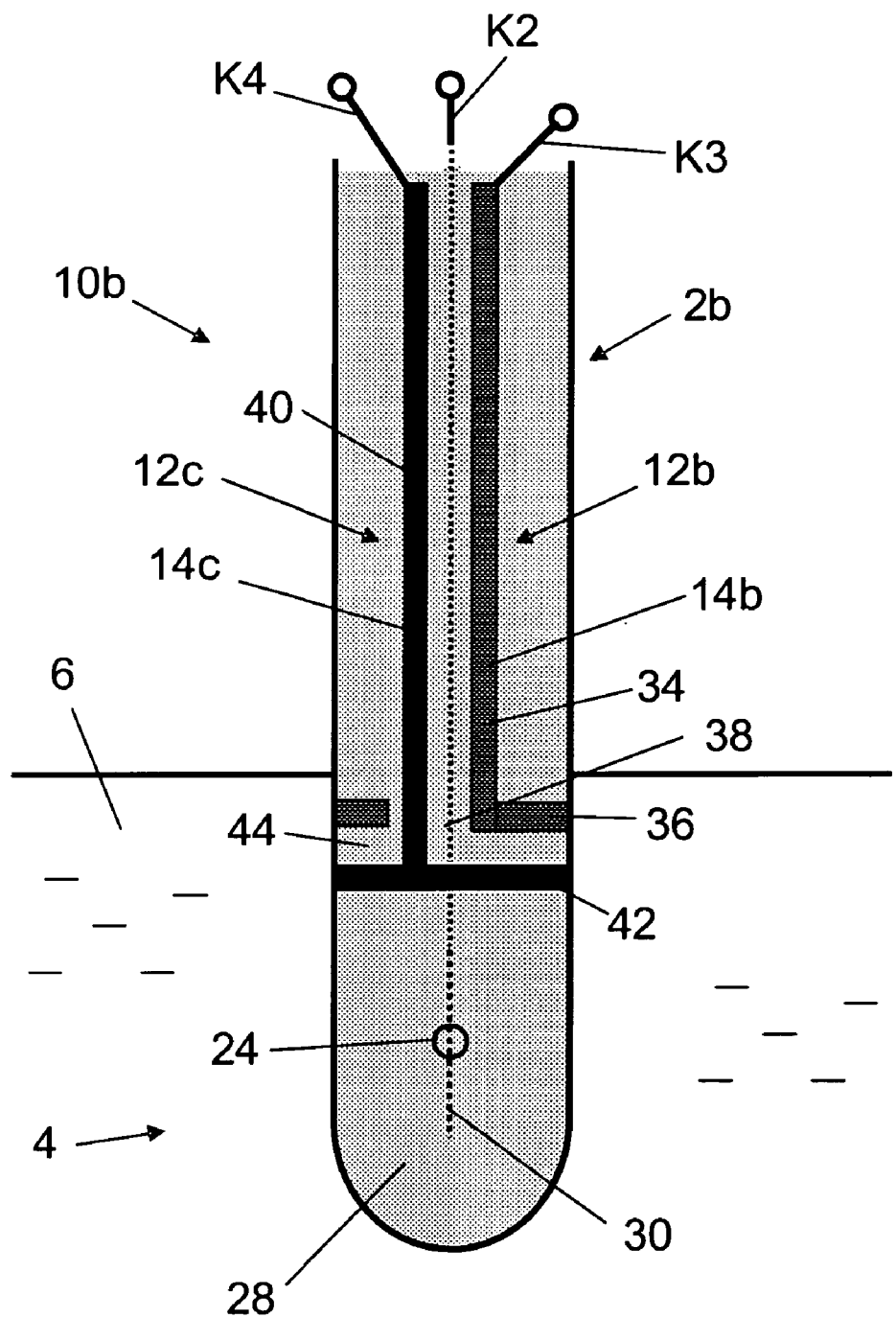
FIG. 3 represents a side view of a measuring probe that is equipped with two additional electrodes.

The measuring probe shown in FIG. 3 includes a reference electrode with a housing 2b whose lower end 4 is immersed in a measuring medium 6. The sensor chamber 10b that is formed by the housing 2b contains a reference electrolyte solution 28 in which a silver wire with a coating layer of silver chloride is immersed, serving as a second conductor element 30. The latter passes through an upper closure part (not shown in detail) of the sensor chamber 10b to the outside where it ends in a reference contact terminal K2. In the immersed area 4, the sensor chamber 10b has a diaphragm 24 in the shape of a circular disk, and there is a refill opening (not specifically illustrated) in the uppermost portion. The measuring probe has a first additional electrode 12b as well as a second additional electrode 12c which are constituted, respectively, by a first coating 14b (shown dark shaded in FIG. 3) and a second coating 14c (shown black in FIG. 3). Both of the coatings 14b, 14c extend from the immersed area 4 to the upper end of the probe housing 2b. The upper end of the first coating 14b is soldered to a first additional contact terminal K3. Analogously, the second coating 14c is soldered to a second additional contact terminal K4.

The first coating 14b includes a first lengthwise coating strip 34 extending from the upper part of the housing to the immersed part 4 and continuing into an upper ring-shaped strip 36 which has an interruption 38. The second coating 14c includes a second lengthwise coating strip 40 extending likewise from the upper part of the housing to the immersed part 4 and continuing into a lower ring-shaped strip 42. As can be seen in FIG. 3, the two lengthwise coating strips 36, 40 extend substantially parallel to each other. The second lengthwise coating strip 40 passes through the interruption 38 of the upper ring-shaped strip 36 to join the lower ring-shaped strip 42. An uncoated zone 44 which is interrupted only by the second lengthwise coating strip 40 separates the two ring-shaped strips 36, 42. Thus, as can be seen in FIG. 3, the first additional electrode 12b is formed by the first lengthwise coating strip 34 and the interrupted upper ring-shaped strip 36, while the second additional electrode 12c is formed by the second lengthwise coating strip 40 and the lower ring-shaped strip 42.

The following method has proven advantageous for producing the coated measuring probes. The first step is to clean the probe housing which consists preferably of lead-free glass. Next, a thin adhesion-enhancing layer of titanium is deposited using a sputtering technique, with a thickness of e.g., about 5 to 20 nm, preferably about 10 nm. The final step is the application of the actual coating which functions as an additional electrode. Good results are achieved in regard to electrochemical and mechanical properties by using, e.g., platinum with a coating thickness of about 200 nm. A partially transparent coating is obtained with a thinner platinum coating of about 50 nm without any significant loss of other properties.

To perform potentiometric measurements, a measuring probe of the foregoing description is connected to an appropriate measurement converter, specifically by connecting the different contact terminals of the measuring probe to the measurement converter. The following operations can be performed with the measuring probes that have been specifically described and illustrated herein:

a) Measurement of the potential between K1 and K2 (FIG. 1): measurement of the pH value;
b) Measurement of the resistance between K1 and K3 (FIG. 1): measurement of the glass membrane resistance;
c) Measurement of the resistance between K2 and K3, or between K2 and K4 (FIGS. 1 to 3): measurement of the diaphragm resistance;
d) Measurement of the potential between K3 and K2 (FIGS. 1 to 3): measurement of a redox potential in the measuring solution (additional electrode of platinum), or measurement of a metal ion concentration in the measuring solution (additional electrode of corresponding metal);
e) Setting a defined potential at K3 (FIGS. 1 to 3): setting the measuring solution at ground potential or equalizing it with another potential;
f) Resistance measurement between K3 and K4 (FIG. 3): determining the electrical conductivity of the measuring solution.

What is claimed is:

1. A probe for potentiometric measurements in a measuring solution or in a process solution, comprising:
a housing formed of an electrically insulating material, an outer portion of the housing adapted to be immersed in the solution, a glass membrane located in the immersible portion and at least one hollow space of the housing containing a half-cell element that defines a first electrode;

at least one additional electrode, defined by an electrically conductive coating attached to the housing adapted to be immersed in the measuring solution, each additional electrode arranged on the immersible portion exclusive of the glass membrane; and at least one contact terminal, each contact terminal corresponding with and connected to one of the additional electrodes, each contact terminal arranged outside of the immersible portion.

2. The probe of claim 1, wherein:
each said contact terminal is soldered to the corresponding coating.

3. The probe of claim 2, wherein:
the coating substantially surrounds the entire housing.

4. The probe of claim 3, wherein:
the coating is at least partially transparent.

5. The probe of claim 4, wherein:
the electrically insulating material comprises glass.

6. The probe of claim 5, wherein:
the coating is applied by deposition from the gaseous phase.

7. The probe of claim 6, wherein:
the coating comprises platinum, gold or palladium.

8. The probe of claim 7, further comprising:
a layer for enhancing adhesion of the coating to the housing, interposed between the coating and the housing.

9. The probe of claim 8, wherein the adhesion layer comprises:
a metal selected from the group consisting of: titanium, chromium, molybdenum, tantalum, and tungsten.

10. The probe of claim 7, wherein:
the half-cell element is configured as a measuring electrode.

11. The probe of claim 7, wherein:
the half-cell element is configured as a reference electrode.

12. The probe of claim 7, wherein:
the probe is configured as a single-rod measuring chain.

13. The probe of claim 12, wherein:
first and second additional electrodes are located in different areas of the immersible portion and are respectively connected to first and second contact terminals.

14. The probe of claim 1, wherein:
the coating substantially surrounds the entire housing.

15. The probe of claim 1, wherein:
the coating is at least partially transparent.

16. The probe of claim 1, wherein:
the electrically insulating material is glass.

17. The probe of claim 1, wherein:
the coating is applied by deposition from the gaseous phase.

18. The probe of claim 1, wherein:
the coating comprises platinum, gold or palladium.

19. The probe of claim 1, further comprising:
a layer for enhancing adhesion of the coating to the housing, interposed between the coating and the housing.

20. The probe of claim 1, wherein:
the half-cell element is configured as a measuring electrode.

21. The probe of claim 1, wherein:
the half-cell element is configured as a reference electrode.

22. The probe of claim 1, wherein:
the probe is configured as a single-rod measuring chain.

23. A device for performing potentiometric measurements, comprising:
a measuring probe as defined in claim 1;
a measurement converter, adapted for connection to each half-cell element of the measuring probe and to the electrical contact terminal of each additional electrode, the measurement converter comprising at least one of:
a means for setting a defined potential at each additional electrode; and
a means for determining a characteristic electrical quantity between one additional electrode and another part of the device.

24. A method for monitoring a probe for potentiometric measurements, comprising the steps of:
providing a device for potentiometric measurements as defined in claim 23; and
measuring a characteristic electrical quantity between one additional electrode and another part of the device.

25. The method of claim 24, further comprising the step of:
setting a defined electrical potential at the additional electrode by means of the measurement converter.

26. The method of claim 24, further comprising the steps of:
configuring one said half-cell element as a reference electrode, and
performing a resistance measurement between the reference electrode contact terminal and the additional electrode contact terminal while the measurement converter is connected to the respective contact terminals, to determine the resistance of a diaphragm in the housing.

27. The method of claim 24, further comprising the steps of:
configuring one said half-cell element as a measuring electrode, and
performing a resistance measurement between the contact terminal of said measuring electrode and the additional electrode contact terminal while the measurement converter is connected to the respective contact terminals to determine the resistance of the glass membrane of the housing.

28. The probe of claim 1, wherein:
the glass membrane comprises pH glass.

29. The probe of claim 1, further comprising:
a diaphragm located in the immersible portion, exclusive of the electrically conductive coating.

* * * * *

UNITED STATES PATENT AND TRADEMARK OFFICE
CERTIFICATE OF CORRECTION

| | | |
|---|---|---|
| PATENT NO. | : 7,176,692 B2 | Page 1 of 1 |
| APPLICATION NO. | : 11/157366 | |
| DATED | : February 13, 2007 | |
| INVENTOR(S) | : Adami et al. | |

It is certified that error appears in the above-identified patent and that said Letters Patent is hereby corrected as shown below:

In column 8, line 13, please delete "adapted for connection to each" and insert -- adapted to be connected to each --.

Signed and Sealed this

Twenty-fourth Day of April, 2007

JON W. DUDAS
*Director of the United States Patent and Trademark Office*